United States Patent [19]
Robert et al.

[11] Patent Number: 5,475,451
[45] Date of Patent: Dec. 12, 1995

[54] OPHTHALMOLOGIC APPARATUS

[75] Inventors: Yves Robert, Susenbergstrasse 24, Ch-8044, Zürich; Franz Papritz, Niederscherli; Phillip Hendrickson, Basel, all of Switzerland

[73] Assignee: Yves Robert, Zürich, Switzerland

[21] Appl. No.: 182,801

[22] Filed: Jan. 14, 1994

[30] Foreign Application Priority Data

Jan. 28, 1993 [CH] Switzerland ............................. 249/93

[51] Int. Cl.⁶ .............................. A61B 3/12; A61B 3/13; A61B 3/15
[52] U.S. Cl. .......................... 351/208; 351/205; 351/214; 351/221
[58] Field of Search ................................... 351/205, 206, 351/207, 208, 211, 213, 214, 220, 221

[56] References Cited

U.S. PATENT DOCUMENTS

| | | | |
|---|---|---|---|
| 4,439,024 | 3/1984 | Ito | 351/207 |
| 4,452,517 | 6/1984 | Kohayakawa | 351/206 |
| 4,572,627 | 2/1986 | Madate et al. | 351/206 |
| 4,662,731 | 5/1987 | Robert et al. | 351/214 |

FOREIGN PATENT DOCUMENTS 662261 9/1987 Switzerland.

Primary Examiner—William L. Sikes
Assistant Examiner—David R. Parsons
Attorney, Agent, or Firm—Martin A. Farber

[57] ABSTRACT

An ophthalmologic apparatus for repeated optical or photometric examination of the fundus or another portion of a patient's eye has an illuminating unit with a light source for a microscope. The optical axis of the microscope can be repeatedly moved to one and the same position relative to a beam of radiation issuing from the center of curvature of the external surface of the cornea in a patient's eye with assistance from a positive field lens which is adjustable with the microscope and acts not unlike an ophthalmoscopic lens for indirect ophthalmoscopy. The lens projects for the microscope a real intermediate image of the selected portion of a patient's eye in an intermediate plane adjacent that focal point of the lens which is remote from the patient's eye. An illuminated or radiation emitting marker is provided at that side of the intermediate plane which faces away from the lens and close to the optical axis of the microscope. The aforementioned components of the apparatus are jointly adjustable by the person in charge along one, two or all three axes which intersect and are inclined relative to each other. Such adjustment is carried out until the intermediate plane receives a sharp image of the selected portion of a patient's eye. A selected portion of the intermediate plane (namely a portion which is observable through the microscope) provides for the microscope a sharp image of the illuminated marker with assistance from a patient's eye in that the external surface of the cornea performs the function of a spherical mirror.

20 Claims, 1 Drawing Sheet

OPHTHALMOLOGIC APPARATUS

BACKGROUND OF THE INVENTION

The invention relates to improvements in ophthalmologic apparatus in general, and more particularly to improvements in apparatus for optical and photometric examination of patients' eyes. Still more particularly, the invention relates to improvements in ophthalmologic apparatus wherein an illuminating unit furnishes light for a second (viewing) unit which serves to permit an examination of a selected portion (particularly the fundus) of a patient's eye.

Heretofore known ophthalmologic apparatus of the above outlined character exhibit the drawback that, if a patient's eye is to be reexamined once or at certain intervals, the physician in charge cannot repeatedly select one and the same position of the center of curvature of the front surface of the cornea or the optical axis of a patient's eye with reference to the apparatus and/or vice versa. A conventional ophthalmologic apparatus is disclosed, for example, in Swiss Pat. No. 622 261. On the other hand, repeated selection of one and the same position of a patient's eye relative to an ophthalmologic apparatus is not only desirable but necessary if a physician is to successfully compare the results of one or more earlier examinations with those of a subsequent examination. As a rule, the head of a patient is affixed to a conventional support. The patient thereupon focusses the eye to be examined upon a reference mark which is projected into the path of rays passing through a microscope. The apparatus is adjustable in three different directions (along the X, Y and/or Z axis), and the person in charge of the examination shifts the apparatus with reference to the eye in the direction(s) of one or more axes until such person discerns a sharp image of the fundus or another part of the eye which requires examination. As mentioned above, conventional apparatus cannot be readily moved exactly to the same position as during one or more earlier examinations. This causes the development of different reflections of light during successive examinations which, in turn, results in inaccurate measurements of brightness and, due to the lack of reproducibility, the thus obtained measurement values are often totally useless to the physician in charge.

OBJECTS OF THE INVENTION

An object of the invention is to provide an ophthalmologic apparatus which can be repeatedly moved to one and the same position with respect to a patient's eye.

Another object of the invention is to provide an ophthalmologic apparatus which can be repeatedly moved to one and the same position with respect to the center of curvature of the front surface of the cornea in a patient's eye.

A further object of the invention is to provide a novel and improved illuminating unit for use in the above outlined ophthalmologic apparatus.

An additional object of the invention is to provide a novel and improved viewing unit for use in an apparatus of the above outlined character.

Still another object of the invention is to provide the above outlined apparatus with novel and improved means for repeatedly locating the illuminating and viewing units in one and the same position relative to a patient's eye irrespective of the length of intervals between successive examinations of such eye.

A further object of the invention is to provide a novel and improved method of adjusting the position of the above outlined ophthalmologic apparatus relative to the eye of a patient.

Another object of the invention is to provide an apparatus which can be utilized by an eye surgeon, for example, to properly position a portion of a doner's eye and a portion of a receiver's eye during transplantation of cornea with assistance from an operational microscope.

An additional object of the invention is to provide an apparatus which can be repeatedly and highly accurately positioned with reference to the optical axis of a patient's eye.

Still another object of the invention is to provide the above outlined ophthalmologic apparatus with a novel and improved system of diaphragms.

A further object of the invention is to provide the above outlined apparatus with novel and improved means for furnishing a sharp image of the fundus or another selected portion of a patient's eye.

Another object of the invention is to provide an apparatus whose manipulation is simple and which can be rapidly and accurately located in an optimum position for examination of an eye as often as desired and at such intervals as desired or necessary.

SUMMARY OF THE INVENTION

The invention resides in the provision of an ophthalmologic apparatus for optical and photometric examination of a patient's eye. The improved apparatus comprises an illuminating unit for the patient's eye, a second unit which serves for viewing a selected portion (particularly the fundus) of the patient's eye, and a positive front lens disposed between the patient's eye and the second (viewing) unit to provide for the second unit a real intermediate image of the selected portion of the patient's eye in an intermediate plane which is located at a focal plane of the lens. The lens is located between the focal plane and the patient's eye, and the intermediate plane is located between the lens and a radiation emitting marker. The apparatus further comprises means for jointly adjusting the two units and the lens relative to the patient's eye to provide in the intermediate plane a sharp image of the selected portion of the patient's eye and to establish for the second unit—in conjunction with a spherical mirror constituted by a front surface of a cornea of the patient's eye—a sharp image of the radiation emitting marker in a predetermined portion of the intermediate plane. The positive front lens can constitute an ophthalmoscopic lens for indirect ophthalmoscopy, and the radiation emitting marker is preferably located at least close to the optical axis of the front lens.

The apparatus can further comprise a two-dimensionally adjustable reference point which is disposed in the intermediate plane and is visible to the patient's eye.

The second (viewing) unit can include a three-dimensionally adjustable microscope which images the selected portion of the patient's eye in a first plane observable through an ocular of the second unit and in a second plane. Such apparatus preferably further comprises a measuring unit having at least one photodetector serving to generate in the second plane signals denoting the intensity of radiation which is reflected by the selected portion of the patient's eye.

The means for generating an image of the radiation emitting marker in the intermediate plane can include an aperture diaphragm disposed at an axis of the illuminating unit.

The adjusting means of the improved apparatus can include a support for the second (viewing) unit and for the lens. The second unit and the lens are jointly adjustable relative to or with the support in the direction of at least one of three mutually inclined axes X, Y and Z.

The adjusting means can further include means for moving the front lens in the direction of the optical axis of the second unit. Such apparatus preferably further comprises a properly graduated scale or other suitable means for indicating the extent of adjustment of the front lens in the direction of such optical axis.

Still further, the apparatus can comprise a partially transmitting filter extending into the field of view of the second unit in the region of the intermediate plane.

The second unit can further comprise a reticle with a plurality of crossed hairs in the aforementioned first plane. For example, the reticle can comprise two crossed hairs each of which defines a picture point.

The aforementioned aperture diaphragm can be disposed at an axis of the illuminating unit, and the latter includes a source of light (e.g., an incandescent lamp or halogen lamp). A filter diaphragm can be installed between the light source and the aperture diaphragm, and such filter diaphragm can include a partially transmitting portion having a first zone of lesser light transmissivity and two second zones of greater light transmissivity. The filter diaphragm is or can be operatively connected with the illuminating unit in such a way that an eye of an observer (e.g., a physician) of the second unit discerns the center of each of the two second zones in register with one of the aforementioned two crossed hairs forming part of the reticle in the second unit. The partially transmitting portion of the filter diaphragm is or can be elongated and then extend transversely of the field of view of the second unit.

The aperture diaphragm and/or the filter diaphragm can be releasably coupled to the illuminating unit. The latter can form part of a slit lamp, and the second unit can be coupled to the illuminating unit.

The measuring unit can include two photodetectors which are disposed in the aforementioned second plane and each such photodetector registers with one of the two crossed hairs to furnish signals which denote the intensity of light at the crossed hairs. Such measuring unit can further comprise means for furnishing a quotient of the two signals. The furnishing means can include or can be connected with a display for the quotient of the signals. The measuring means of such apparatus can further comprise means for recording the examined regions of the selected portion of the patient's eye and of the examined points of such regions. It is further possible to provide a CCD camera for recording the image in the aforementioned second plane, and the measuring unit of such apparatus can include means for automatically and selectively measuring the characteristics of selected portions of the image in one of the first and second planes, for generating signals denoting the measured characteristics and for evaluating and recording and/or displaying the signals.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawings.

DESCRIPTION OF PREFERRED EMBODIMENTS

Figure 1:
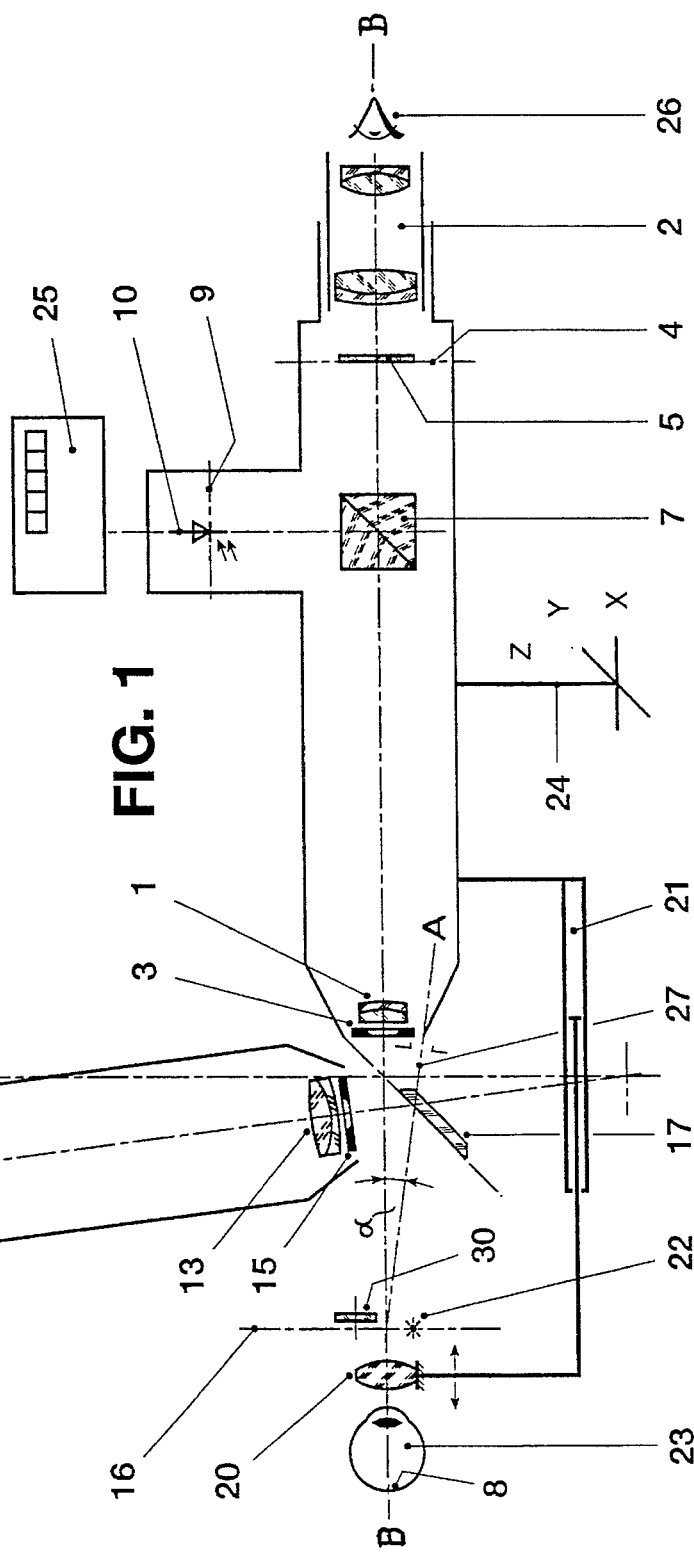
FIG. 1 is a diagrammatic view of an ophthalmologic apparatus which embodies one form of the invention.

The improved apparatus comprises a viewing unit including a horizontal monocular microscope with a magnification factor of between 10 and 20. The microscope comprises an achromatic objective 1 and an ocular 2. A diaphragm 3 of the microscope is installed in front of the objective 1, i.e., between the objective and the eye 23 of a patient. The dimensions of the aperture which is defined by the diaphragm 3 determine the area which can be observed by a physician's or a nurse's eye 26 by looking through the tube of the microscope constituting the viewing unit of the improved ophthalmologic apparatus. A plate-like reticle 5 of the microscope is disposed in a (first) plane 4 which is located between the objective 1 and the ocular 2 of the microscope. The frame of the reticle 5 determines the field of view of the microscope. The reticle 5 includes two reference lines or crossed hairs 6 (see FIG. 2) denoting two image points at a requisite horizontal distance from each other. A beam splitting cube 7 is installed between the objective 1 and the reticle 5 to direct a portion of light reflected by the fundus 8 of the patient's eye 23 laterally into a second plane or image plane 9 so that the thus directed portion of reflected light can be monitored for the purposes of measurement. The second plane or image plane 9 is disposed at right angles to the plane of FIG. 1 and contains two spaced-apart photodiodes 10 which are disposed one behind the other (as viewed in FIG. 1) so that only one such diode is seen in FIG. 1 of the drawings. Each of the photodiodes 10 has a relatively small measuring surface. The photodiodes 10 can be centered in such a way that their locations correspond exactly to the image points defined on the reticle 5 by the two crossed hairs 6.

Figure 2:
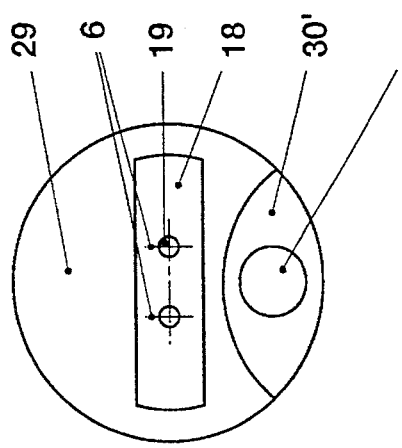
FIG. 2 is a plan view of the field of view of the ocular forming part of the viewing unit in the ophthalmologic apparatus of FIG. 1.

The ophthalmologic apparatus further comprises an illuminating unit including a light source 11 (e.g., an incandescent light bulb or a halogen lamp), an achromatic projector lens 13 and a condenser lens 12 between the light source 11 and the lens 13. The illuminating unit including the just described parts 11, 12 and 13 is preferably further combined with a filter diaphragm 14 which is installed between the lenses 12, 13, and an aperture diaphragm 15 in front of the projection lens 13. The illuminating unit including the parts 11 to 13 is preferably mounted in such a way that a reflected part of its optical axis A—A intersects the optical axis B—B of the microscope in an intermediate plane 16 of the microscope at an angle alpha. It is presently preferred to install the illuminating unit including the parts 11 to 13 at a level above the microscope and to reflect the beam of light furnished by the source 11 at a front surface mirror 17 which latter is fixedly mounted at a level below the optical axis B—B. The light beam which issues from the source 11 and is reflected by the mirror 17 propagates itself upwardly and makes with the optical axis B—B the aforementioned acute angle alpha. The reflected beam of light issuing from the source 11 crosses the axis B-B in the intermediate plane 22. The selected angle of incidence of light (i.e., the angle alpha) and proper dimensioning of the diaphragms 3 and 15 ensure that undesirable reflected light (caused primarily by reflection at the surfaces of refractive media) cannot reach the path of radiation passing through the microscope, especially from the path of radiation which is to be measured by the improved apparatus. The optical elements of the illuminating unit including the parts 11 to 13 are designed in such a way that the projection lens 13 images the filter diaphragm 14 in the intermediate plane 16. The diaphragm 14 is provided with an opaque film which can be applied thereto by sputtering, by metallizing or in accordance with any other suitable procedure, and serves to limit the size or area of the illuminated field of view 18 (FIG. 2). Similar results can be obtained by appropriate dimensioning of the diaphragm 14. When projected into the intermediate plane 22, the field of view 18 preferably assumes a rectangular shape (as shown in FIG. 2) with the longer sides extending horizontally or at least substantially horizontally. The illuminated field 18 contains a filtering layer which acts not unlike a long pass filter by permitting passage of red light in the wavelength range of 600 nanometers or longer (reference may be had to long pass filters known as Wrattenfilter No. 25). The film or layer of filtering material does not cover the entire illuminated field 18; it leaves uncovered two relatively small circular zones or portions 19 each of which contains one of the crossed hairs 6 of the reticle 5 forming .part of the microscope. The zones 19 permit passage of "white" light, and the purpose of such zones is to prevent a patient's eye 23 from being unduly affected by glare while, at the same time, facilitating orientation by the person in charge (see the eye 26 in FIG. 1).

The improved apparatus further comprises an aspherical positive front lens 20 which is traversed by an extension of the optical axis B—B of the microscope and is installed in front of the intermediate plane 16, namely between such plane and the eye 23 of a patient. The lens 20 is or can be of the type known as an ophthalmoscopic lens for indirect ophthalmoscopy. The positioning of the lens 20 is such that its rear focal plane (i.e., that which is more distant from a patient's eye 23) is located primarily in, or at least close to, the intermediate plane 16. A straight line guide 21 (shown as a cylinder and piston assembly) can be provided to permit a certain movement of the lens 20 (e.g., in the range of a few millimeters) forwardly or rearwards as seen in the direction of the axis B—B.

A fixation mark 22 is provided in the intermediate plane 16 and is shiftable two-dimensionally in a plane extending at right angles to the axis B—B of the microscope. The fixation mark 22 furnishes a reference point to the eye 23 of a patient.

The improved apparatus further comprises a support or base 24 which is or can be designed in such a way that the aforementioned components of the ophthalmologic apparatus can be adjusted three-dimensionally, namely in the direction of each of the three mutually inclined and intersecting axes X, Y and Z. The support or base 24 can be mounted or positioned on a suitable carrier (e.g., a table, not shown) and is or can be moved with the component parts of the two units and with other constituents of the improved apparatus in the direction of the axis X, Y and/or Z.

The photodiodes 10 transmit signals which are processed in a circuit 25. This circuit and the photodiodes 10 can be said to constitute a measuring unit of the improved ophthalmologic apparatus. The output of the circuit 25 can transmit digital signals which are indicative of the (processed) signals furnished by the photodiodes 10, and such circuit preferably includes or is connected with a suitable display.

The operation of the heretofore described ophthalmologic apparatus is as follows:

The pupil of the eye 23 to be examined is dilated in good time prior to examination. The person in charge adjusts the ocular 2 of the microscope for her or his eye 26 free of accommodation upon the built-in reticle 5. As is customary in apparatus of the type to which the present invention pertains, the patient is seated and the chin and the forehead of her or his head are caused to rest on a conventional head support, not shown. The person in charge thereupon manipulates the controls of the adjusting means including the support or base 24 to move the front lens 20 in front of and a distance of a few millimeters from the patient's eye 23. If the centering is relatively satisfactory, the fundus 8 of the eye 23 is already observable by the eye 26 looking through the microscope including the ocular 2. Depending upon the nature of the disease of or other damage to the eye 23, (e.g., anomaly of refractive power of the eye), the front lens 20 is to be shifted in the direction of the axis B—B. If the patient suffers from myopia, the lens 20 is to be shifted away from the eye 23. On the other hand, if the patient suffers from hyperopia, the lens 20 will be adjusted in a direction toward the eye 23. The adjustment is satisfactory, i.e., the adjusting operation can be terminated, when the eye 26 of the person in charge sees a sharp image of the retina in the eye 23. At the same time, such adjustment ensures that the patient (a) can discern a sharp image of the adjustable reference point (fixation mark) 22 in the intermediate plane 16 and (b) can follow movements of the reference point 22 in the plane 16. Such movements are effected by the person whose eye 26 looks into the ocular 2 of the microscope. The above outlined steps render it possible to rapidly and reliably orient the improved apparatus and a patient's eye 23 relative to each other in such a way that the person in charge can move the apparatus to a position in which the selected portions of the retina in the eye 23 register with those picture points which are determined by the photodiodes 10. The photodiodes 10 thereupon measure the intensity of light which is being reflected by selected portions of the retina in the eye 23, and such signals are evaluated by the circuit 25 so that the latter can present the results of evaluation on the display (not shown). For example, the circuit 25 can be designed to furnish a quotient of signals denoting the brightness values determined by the two photodetectors 10. The higher value is the dividend and the lower value is the denominator of the quotient. Such quotient is thereupon made visible on the screen of the display in the circuit 25 of the measuring unit further including the photodiodes 10. The quotient is indicative of the ability of the optical media of the eye 23 to transmit contrasts.

An important prerequisite which must be satisfied in order to obtain accurately reproducible results of measurements is an absolutely reliable positioning or orientation of the improved apparatus and of a patient's eye 23 relative to each other. In order to even more reliably meet such requirements, the improved apparatus embodies certain additional features which are described below.

In order to simplify the description, it is now assumed that the eye 23 of a patient is an emmetropic eye. When the front lens 20 is placed adjacent the eye 23, it is assumed that the paths of light rays between the eye 23 and the lens 20 are parallel to each other. This brings about the advantage that slight displacement of the ophthalmologic apparatus in the direction of the axis X, Y and/or Z does not entail any shifting and/or reduction of sharpness of the image in the eyepiece. Otherwise stated, vignetting is the only limit which is imposed upon the movability of the apparatus relative to the eye 23. Depending on the depth adjustment, a movement of the apparatus transversely of the eye 23 at first entails a reduction of brightness in the left-hand or in the right-hand portion of the image. An intermediate position of the apparatus relative to the eye 23 ensures that the person in charge arrives at an accurately determined depth position so that the brightness of the entire image is reduced uniformly in response to a transverse movement of the apparatus relative to the eye 23. On the other hand, the cones of rays which are necessary for proper observation of the eye 23 and for monitoring by the detectors 10 are considerably narrower than the space which is available due to dilution of the pupil of the eye 23. Different results of measurement are likely to be obtained if the next-following examination or examinations involve the examination of selected portions having different turbidity or cloudiness, i.e., different transparencies in the media of the eye. Accordingly, reliably reproducible results of measurements can be obtained if the apparatus is designed to further ensure such adjustment relative to an eye 23 that the position relative to the axis of the eye as well as relative to the center of curvature of the external surface of the cornea of the eye are exactly the same as during each preceding examination. In other words, it is necessary to properly position the apparatus in the space of the eye media.

This is accomplished by the provision of the aperture diaphragm 15 in the illuminating unit, and more specifically by a radiation emitting marker 27, which is a reflected image of the diaphragm 15 as well as by utilizing the front surface of the cornea forming part of a patient's eye 23. The front surface of the cornea of the eye 23 acts not unlike a spherical mirror.

Let it now be assumed that the patient's eye 23 is not maintained in the position of FIG. 1. The front lens 20 than establishes a bright smaller-scale image of the aperture diaphragm 15 at a location slightly outside of its front focal point. When such image of the diaphragm 15 is projected onto the eye 23, it can be said to constitute a secondary light source for illumination of the retina. Actually, the retina receives a sharp image of the illuminated field 18 of the filter diaphragm 14 with a red filter film and within the boundaries for the field.

If the ophthalmologic apparatus is positioned in front of the eye 23 in such a way that the aforementioned smaller-scale image of the aperture diaphragm 15 impinges upon the external surface of the cornea approximately midway between the apex and the center of curvature, a portion of light is reflected by the external surface of the cornea (which acts as a spherical mirror). The reflected light is a bundle of parallel rays which impinge upon the front lens 20. Thus, an image 15' (see FIG. 2) of the diaphragm 15 is provided in the rear focal plane of the front lens 20, and more specifically in the intermediate plane 16. By properly centering the apparatus, the image 15' of the diaphragm 15 can be observed through the microscope as a very bright and sharply outlined circular image. Such image can be provided again and again, always at the same locus of the field of view 29.

The image 15' of the diaphragm 15 is quite bright so that it could possibly interfere with radiation which is monitored by the photodetectors 10, i.e., the image 15' could adversely influence the characteristics of signals which are being transmitted for evaluation and display to the circuit 25. This is avoided by centering the apparatus in such a way the image 15' of the diaphragm 15 appears at the margin of the field of view 29. It is presently preferred to project the image 15' close to the lowermost part of the marginal portion of the field of view 29 (see FIG. 2), provided that the microscope is not equipped with an image erecting system. The image 15' is adjacent the uppermost part of the marginal portion of the field of view 29 if the microscope is equipped with image erecting means.

The brightness of the image 15' can be reduced considerably by employing a light intensity reducing filter 30 which is positioned at the intermediate plane 16 above the optical axis B—B. The filter 30 has a circular outline and extends in part into the field of view 29 of the microscope. The arrangement is preferably such that the extent of overlap between the filter 30 and field of view 29 equals or is close to approximately one-third of the diameter of the field of view 29. A person looking into the ocular 2 of the microscope sees a slightly blurred (unsharp) image of the filter 30. The "dark" zone 30' of the field of view 29 is bounded by two circular arcs.

The fixation marker 22 can be omitted if the apparatus is expected to merely ensure a reproducible positioning with reference to the center of curvature of the front surface of the cornea in a patient's eye.

The improved apparatus can constitute a self-sustaining assembly. Alternatively, the improved apparatus can be utilized as a permanent or separable attachment to another apparatus, such as a standard slit lamp apparatus which is available in the office of each ophthalmologist as well as in the eye clinic of each hospital. The illuminating means of a well known and widely used slit lamp apparatus can be equipped with the aforementioned filter for red light; this renders it possible to dispense with an integrated illuminating arrangement. A further advantage of the combination of such modified slit lamp apparatus with the improved ophthalmologic apparatus is that it can dispense with the mirror 17.

The measuring unit including the photodetectors 10 and the circuit 25 can be replaced with a CCD camera or an analogous piece of equipment which is provided with an automatic signal evaluating circuit. The evaluating circuit of the CCD camera or its equivalent carries out selective measurements at a plurality (e.g., two) of most important parts of the image. For example, the camera can photographically record the examined part of parts of the retina simultaneously with an indication of the location of the measured part(s).

The improved apparatus can be utilized for the examination of a patient's eye in order to determine the presence or absence of damage to and/or other abnormalities, as well as to facilitate and speed up eye surgery, e.g., for transplanting a cornea from a donor to a receiver. The microscope which is customarily employed for eye surgery can be modified to constitute a microscope of the above outlined character, or the microscope of the improved ophthalmologic apparatus can be utilized in addition to a standard microscope.

The fixation marker 22 constitutes a highly desirable but optical feature of the improved apparatus. As already described hereinabove, the marker 22 renders it possible to even further enhance the possibility of accurately positioning the apparatus relative to the optical axis of one and the same eye at desired intervals and as often as necessary.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. An ophthalmologic apparatus for optical and photometric examination of a patient's eye, comprising an illuminating unit for the patient's eye; a second unit for viewing a selected portion of the patient's eye; a positive front lens disposed between the patient's eye and the second unit to provide for the second unit a real intermediate image of the selected portion of the patient's eye in an intermediate plane located at a focal plane of said lens, said lens being located between said focal plane and the patient's eye and said intermediate plane being located between said lens and a radiation emitting marker; and means for jointly adjusting said units and said lens relative to the patient's eye to provide in said intermediate plane a sharp image of the selected portion of the patient's eye and to establish for the second unit, in conjunction with a spherical mirror constituted by a front surface of a cornea of the patient's eye, a sharp image of the marker in a predetermined portion of the intermediate plane.

2. The apparatus of claim 1, wherein said positive front lens is an ophthalmoscopic lens for indirect ophthalmoscopy and said marker is located at least close to the optical axis of said lens.

3. The apparatus of claim 1, further comprising a two-dimensionally adjustable reference point disposed in said intermediate plane and being visible to the patient's eye.

4. The apparatus of claim 1, wherein said second unit includes a three-dimensionally adjustable microscope which images the selected portion of the patient's eye in a first plane observable through an ocular of the second unit and a second plane, and further comprising a measuring unit including at least one photodetector arranged to generate in said second plane signals denoting the intensity of radiation which is reflected by the selected portion of the patient's eye.

5. The apparatus of claim 1, further comprising means for generating said marker in said intermediate plane, including an aperture diaphragm at an axis of said illuminating unit.

6. The apparatus of claim 1, wherein said adjusting means includes a support for said second unit and said lens, said second unit and said lens being jointly adjustable relative to said support in the direction of at least one of three mutually inclined intersecting axes.

7. The apparatus of claim 1, wherein said second unit has an optical axis and said adjusting means includes means for moving said lens in the direction of said axis.

8. The apparatus of claim 7, further comprising means for indicating the extent of adjustment of said lens in the direction of said optical axis.

9. The apparatus of claim 1, wherein said second unit has a field of view and further comprising a partially transmitting filter extending into said field of view in the region of said intermediate plane.

10. The apparatus of claim 1, wherein said second unit includes a three-dimensionally adjustable microscope which images the selected portion of the patient's eye in a predetermined plane observable through an ocular of the second unit, said second unit further comprising a reticle with a plurality of crossed hairs in said predetermined plane.

11. The apparatus of claim 10, wherein said reticle comprises two crossed hairs each of which determines a picture point.

12. The apparatus of claim 1, further comprising means for generating said marker in said intermediate plane, including an aperture diaphragm at an axis of said illuminating unit, said illuminating unit including a source of light and further comprising a filter diaphragm disposed between said source and said aperture diaphragm and including a partially transmitting portion having a first zone of lesser light transmissivity and two second zones of greater light transmissivity, said second zones having centers and said filter diaphragm being operatively connected with said illuminating unit in such a way that an eye of an observer of said second unit discerns each of said centers in register with one of two crossed hairs forming part of a reticle in said second unit.

13. The apparatus of claim 12, wherein said partially transmitting portion is elongated and extends transversely of a field of view of said second unit.

14. The apparatus of claim 1, further comprising means for generating said marker in said intermediate plane including an aperture diaphragm at an axis of said illuminating unit, said diaphragm being adapted to be coupled to said illuminating unit.

15. The apparatus of claim 14, further comprising a filter diaphragm disposed between a light source of said illuminating unit and said aperture diaphragm and being adapted to be coupled to said illuminating unit.

16. The apparatus of claim 1, wherein said illuminating unit forms part of a slit lamp and said second unit is adapted to be coupled to said illuminating unit.

17. The apparatus of claim 1, wherein said second unit includes a microscope which images the selected portion of the patient's eye in a first plane observable through an ocular of the second unit and a second plane, said second unit further including a reticle having two crossed hairs in said second plane and further comprising a measuring unit having two photodetectors disposed in said second plane and each registering with one of said crossed hairs to furnish signals denoting the intensity of light at said crossed hairs, said measuring unit further comprising means for furnishing a quotient of said signals.

18. The apparatus of claim 17, wherein said furnishing means includes a display for the quotient of said signals.

19. The apparatus of claim 17, wherein said measuring means further comprises means for recording the examined regions of the selected portion of the patient's eye and of the examined points of said regions.

20. The apparatus of claim 1, wherein said second unit includes a microscope which images the selected portion of the patient's eye in a first plane observable through an ocular of said second unit and a second plane, and further comprising a CCD camera for recording the image in said second plane, and a measuring unit including means for automatically and selectively measuring the characteristics of selected portions of the image in one of said first and second planes, for generating signals denoting said characteristics and for evaluating and recording and/or displaying said signals.

* * * * *